US012642700B2

(12) United States Patent
Bor

(10) Patent No.: US 12,642,700 B2
(45) Date of Patent: Jun. 2, 2026

(54) TREATING EYE CONDITIONS WITH SUBTHRESHOLD FEMTOSECOND LASER PULSES

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 741 days.

(21) Appl. No.: 18/050,385

(22) Filed: Oct. 27, 2022

(65) Prior Publication Data

US 2023/0157889 A1     May 25, 2023

Related U.S. Application Data

(60) Provisional application No. 63/281,511, filed on Nov. 19, 2021.

(51) Int. Cl.
*A61F 9/008* (2006.01)

(52) U.S. Cl.
CPC .. *A61F 9/0084* (2013.01); *A61F 2009/00846* (2013.01); *A61F 2009/00874* (2013.01); *A61F 2009/00897* (2013.01)

(58) Field of Classification Search
None
See application file for complete search history.

(56) References Cited

U.S. PATENT DOCUMENTS

| | | |
|---|---|---|
| 3,780,979 A | 12/1973 | De Guillebon |
| 4,357,088 A | 11/1982 | Pomerantzeff |
| 5,312,396 A | 5/1994 | Feld |
| 5,909,270 A | 6/1999 | Moser |
| 6,142,630 A | 11/2000 | Koester |
| 6,322,556 B1 | 11/2001 | Gwon |
| 6,789,900 B2 | 9/2004 | Van De Velde |
| 7,374,287 B2 | 5/2008 | Van De Velde |
| 7,510,282 B2 | 3/2009 | Ueno |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

"Shinonaga, et al., Formation of periodic nanostructures with femtosecond laser for creation of new functional biomaterials, 2016, Science Direct, pp. 57-61" (Year: 2016).*

(Continued)

*Primary Examiner* — Michael T. Holtzclaw
(74) *Attorney, Agent, or Firm* — Patterson + Sheridan, LLP

(57)     ABSTRACT

In certain embodiments, an ophthalmic laser surgical system for treating a target tissue in an eye includes a target detection system and a laser device. The target tissue has an optical breakdown threshold. The target detection system directs detection beams along a detection beam path towards the target tissue in a vitreous of the eye, and determines a location of the target tissue within the vitreous. The laser device includes a femtosecond laser that generates subthreshold laser pulses that have a pulse energy below the optical breakdown threshold of the tissue. The laser device directs a laser beam comprising the subthreshold laser pulses along a laser beam path towards the target tissue.

20 Claims, 3 Drawing Sheets

(56) References Cited

U.S. PATENT DOCUMENTS

| | | | |
|---|---|---|---|
| 7,520,613 | B2 | 4/2009 | Saito et al. |
| 7,703,922 | B2 | 4/2010 | Van |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 2007/0055221 | A1* | 3/2007 | Lubatschowski ....... A61F 9/008 606/5 |
| 2007/0258094 | A1 | 11/2007 | Zatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0143772 | A1* | 6/2009 | Kurtz ..................... A61F 9/008 606/4 |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0281235 | A1 | 11/2012 | Murata |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0252213 | A1 | 9/2017 | Furuuchi et al. |
| 2017/0326003 | A1 | 11/2017 | Schuele et al. |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0338595 | A1* | 11/2021 | De Smedt ............ A61K 9/0019 |
| 2021/0378507 | A1 | 12/2021 | Wallace |

| | | | |
|---|---|---|---|
| 2021/0386586 | A1 | 12/2021 | Bor |
| 2022/0012459 | A1 | 1/2022 | Schwiegerling |
| 2022/0031511 | A1 | 2/2022 | Charles |
| 2023/0157889 | A1 | 5/2023 | Bor |
| 2023/0381022 | A1* | 11/2023 | Katchinskiy ........... A61F 9/008 |

FOREIGN PATENT DOCUMENTS

| | | | |
|---|---|---|---|
| CN | 108371542 B | 4/2020 | |
| CN | 109196333 B | 12/2020 | |
| CN | 111281651 B | 12/2020 | |
| CN | 112862782 A | 5/2021 | |
| CN | 112587302 B | 6/2021 | |
| CN | 112587304 B | 6/2021 | |
| DE | 19705044 A1 | 8/1998 | |
| DE | 102019007147 A1 | 4/2021 | |
| DE | 102019007148 A1 | 4/2021 | |
| EP | 0770370 A2 | 2/1997 | |
| EP | 1212022 B1 | 3/2005 | |
| EP | 1563785 A1 | 8/2005 | |
| EP | 1638452 B1 | 10/2006 | |
| EP | 1838212 A1 | 10/2007 | |
| EP | 2144552 A1 | 1/2010 | |
| EP | 1928297 B1 | 11/2010 | |
| EP | 2459138 A2 | 6/2012 | |
| EP | 2525706 A2 | 11/2012 | |
| EP | 2898820 A1 | 7/2015 | |
| EP | 3061429 A1 | 8/2016 | |
| EP | 2890340 B1 | 2/2017 | |
| EP | 3459487 A1 | 3/2019 | |
| EP | 3501463 A1 | 6/2019 | |
| EP | 3636137 A1 | 4/2020 | |
| EP | 3861924 A1 | 8/2021 | |
| GB | 2469249 A | 10/2010 | |
| JP | 5767014 B2 | 6/2015 | |
| JP | 2017176558 A | 10/2017 | |
| JP | 6410468 B2 | 10/2018 | |
| JP | 2018196821 A | 12/2018 | |
| JP | 2018196822 A | 12/2018 | |
| JP | 2020022569 A | 2/2020 | |
| JP | 6736304 B2 | 7/2020 | |
| JP | 6839902 B2 | 2/2021 | |
| RU | 2661016 C1 | 7/2018 | |
| RU | 2692666 C1 | 6/2019 | |
| RU | 2695629 C1 | 7/2019 | |
| RU | 2710058 C2 | 12/2019 | |
| RU | 2726468 C1 | 7/2020 | |
| WO | 9958047 A1 | 11/1999 | |
| WO | 0137769 A1 | 5/2001 | |
| WO | 0195791 A1 | 12/2001 | |
| WO | 2007059189 A2 | 5/2007 | |
| WO | 2009033110 A2 | 3/2009 | |
| WO | 2009036104 A2 | 3/2009 | |
| WO | 2009039315 A2 | 3/2009 | |
| WO | 2009059400 A1 | 5/2009 | |
| WO | 2010117386 A1 | 10/2010 | |
| WO | 2014053824 A1 | 4/2014 | |
| WO | 2015131135 A1 | 9/2015 | |
| WO | 2015171793 A1 | 11/2015 | |
| WO | 2016033590 A1 | 3/2016 | |
| WO | 2017062673 A1 | 4/2017 | |
| WO | 2017196306 A1 | 11/2017 | |
| WO | 2017205857 A1 | 11/2017 | |
| WO | 2020074532 A1 | 4/2020 | |
| WO | 2020180729 A1 | 9/2020 | |
| WO | 2020215359 A1 | 10/2020 | |
| WO | 2020216763 A1 | 10/2020 | |
| WO | 2020257711 A1 | 12/2020 | |
| WO | 2021023799 A1 | 2/2021 | |
| WO | 2021049243 A1 | 3/2021 | |
| WO | 2021066047 A1 | 4/2021 | |
| WO | 2021092211 A1 | 5/2021 | |
| WO | 2021183637 A1 | 9/2021 | |
| WO | 2022149028 A1 | 7/2022 | |
| WO | 2023089416 A1 | 5/2023 | |

(56)             References Cited

FOREIGN PATENT DOCUMENTS

| WO | 2023089459 A1 | 5/2023 |
| WO | 2023097391 A1 | 6/2023 |

OTHER PUBLICATIONS

"Huang, et al., Optical Coherence Tomography, PubMed Central, 2015" (Year: 2015).*

Adrian G.H. Podoleanu et al., Combined optical coherence tomograph and scanning laser ophthalmoscope mi nije dostupan besplatno., Electronics Letters, 34 (11), 1998.

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular-Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

D.H.Kelly, "Retinal Inhomogeneity. I. Spatiotemporal Contrast Sensitivity," J. Opt. Sec. Am., pp. 107-113, vol. 1, No. 1 (Jan. 1984).

Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.

Peter G. J. Barten, "Contrast Sensitivity of the Human Eye and its Effects on Image Quality," Chapter 3, pp. 27-40, Model for the spatial contrast sensitivity of the eye, (1999).

Pointer, J. S., & Hess, R. F. "The contrast sensitivity gradient across the human visual field: With emphasis on the low spatial frequency range,", R. F. Vision Research, 29(9), 1133-1151 (1989).

Sebag J et al., Vitreous and Vitreoretinal Interface, Ch. 21, 2015.

Sebag J., Vitreous and Vision Degrading Myodesopsia. Progress in Retinal and Eye Research Nov. 2020;79.

T Ivanova et al, Vitrectomy for primary symptomatic vitreous opacities: an evidence-based review, Eye (Lond) May 2016;30(5):645-55.

Teri T Kleinberg et al., Vitreous substitutes: a comprehensive review, Survey of Ophthalmology, 56 (4), 2011.

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.

Chirag P. Shah, et al., YAG Laser Vitreolysis vs Sham YAG Vitreolysis for Symptomatic Vitreous Floaters a Randomized Clinical Trial, JAMA Ophthalmology, Sep. 2017, 918-923, 135-9.

Ellex Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacities by Light-Induced Vapor Nanobubbles", ACS Nano, vol. 13, No. 7, Jul. 9, 2019, pp. 8401-8416.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

Reece Bergstrom, et al., Vitreous Floaters, National Center for Biotechnology Information, May 21, 2020, 4 pages, Bookshelf ID NBK470420, StatPearls Publishing LLC, online.

Wikipedia Encyclopedia, Floater, Wikipedia Encyclopedia, Mar. 29, 2021, online: https://en.wikipedia.org/wiki/floater?wprov=sfti 1.

Zhang Yunbo et al: "Parallel large-range scanning confocal microscope based on a digital micromirror device", Optik vol. 124, No. 13 (2013), Aug. 4, 2012, pp. 1585-1588.

Damodaran et al., "Digital micromirror device based ophthalmoscope with concentric circle scanning", 2017, pp. 2766-2780, vol. 8, No. 5, Biomedical Optics Express.

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering Gmbh, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/US/en/products/spectralis/ spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, Plos One.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

Sarunic et al., "Instantaneous complex conjugate resolved spectral domain and swept-source OCT using 3×3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim at Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&pr_ref_pid=4513048952866&pr_seq=uniform.

Volk Optical, "Volk Singh Mid-Vitreous Lens", Dec. 20, 2020, accessed on Dec. 20, 2020 from https://www.volk. com/products/singh-mid-vitreous-vitreous-slit-lamp-lens ?_pos=3amp;amp ;_SID=b50c0674famp;amp ;_ ss=I.

Wang et al., "In vivo full range complex Fourier domain optical coherence tomography", Jan. 30, 2007, 054103, vol. 90, Applied Physics Letters.

(56)         References Cited

OTHER PUBLICATIONS

Wojtkowski et al., "Full range complex spectral optical coherence tomography technique in eye imaging", 2002, pp. 1415-1417, vol. 27, No. 16, Optics Letters.

Yasuno et al., "Simultaneous B-M-mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhou et al., "Dual channel dual focus optical coherence tomography for imaging accommodation of the eye", May 25, 2009, pp. 8947-8955, vol. 17, No. 11, Optics Express.

* cited by examiner

TREATING EYE CONDITIONS WITH SUBTHRESHOLD FEMTOSECOND LASER PULSES

TECHNICAL FIELD

The present disclosure relates generally to ophthalmic laser surgical systems, and more particularly to treating eye conditions with subthreshold femtosecond laser pulses.

BACKGROUND

In ophthalmic laser surgery, a surgeon may direct a laser beam into the eye to treat the eye. For example, a laser beam may be directed into the vitreous to treat eye floaters. Eye floaters are clumps of collagen proteins that form in the vitreous. These clumps can disturb vision with moving shadows and distortions. The laser beam may be used to fragment the floaters to improve vision.

BRIEF SUMMARY

In certain embodiments, an ophthalmic laser surgical system for treating a target tissue in an eye includes a target detection system and a laser device. The target tissue has an optical breakdown threshold. The target detection system directs detection beams along a detection beam path towards the target tissue in a vitreous of the eye, and determines a location of the target tissue within the vitreous. The laser device includes a femtosecond laser that generates subthreshold laser pulses that have a pulse energy below the optical breakdown threshold of the tissue. The laser device directs a laser beam comprising the subthreshold laser pulses along a laser beam path towards the target tissue.

Embodiments may include none, one, some, or all of the following features:

The ophthalmic laser surgical system further comprises an xy-scanner. The xy-scanner: receives the detection beams from the target detection system and directs the detection beams along the detection beam path towards an xy-location of a target shadow cast by the target tissue onto the retina of the eye, the xy-location relative to an xy-scanner; and receives the laser beam from the laser device and directs the laser beam along the laser beam path aligned with the detection beam path towards the xy-location of the target shadow.

The pulse energy is 1 to 100 nanojoules (nJ).

The subthreshold laser pulses have a duration of 10 to 500 femtoseconds (fs).

The subthreshold laser pulses have a repetition rate of 1 to 100 megahertz (MHz).

The laser device configured to direct the laser beam comprising the plurality of subthreshold laser pulses by directing 10 to 100 subthreshold laser pulses towards the same spot of the target tissue. The number N of subthreshold laser pulses at the same target spot may be controlled by a repetition rate f of the laser device, an xy-scanning speed v of a laser spot of the laser beam, and a target spot diameter d according to $N=(d*f)/v$.

The laser device comprises a z-focusing component that receives a z-location of the target tissue relative to the retina, and directs a focal point of the laser beam towards the z-location of the target tissue.

The target detection system comprises an xy-location device that provides an xy-location of a target shadow of the target tissue relative to an xy-scanner, and a z-location device that provides a z-location of the target tissue relative to the retina.

The xy-location device comprises a scanning laser ophthalmoscopy (SLO) device.

The z-location device comprises an interferometer device.

The target tissue comprises a vitreous-retinal traction fiber.

The target tissue comprises a vitreous floater.

The laser forms a cloud of low-density free electrons using the subthreshold laser pulses to trigger a chemical reaction that locally disintegrates a portion of the target tissue.

The laser forms singlet oxygen molecules using the subthreshold laser pulses to cause a chemically reaction within a portion of the target tissue.

The laser causes a multiphoton chemical reaction using the subthreshold laser pulses to locally disintegrate a portion of the target tissue.

The laser cause a supersonic thermoelastic wave using the subthreshold laser pulses to locally disintegrate a portion of the target tissue.

In certain embodiments, an ophthalmic laser surgical system for treating a target tissue in an eye comprises a target detection system and a laser device. The target detection system directs detection beams along a detection beam path towards the target tissue in the vitreous of the eye and determines the location of the target tissue. The laser device comprises a femtosecond laser that generates subthreshold laser pulses. The subthreshold laser pulses have a pulse energy below the optical breakdown threshold of the target tissue, e.g., 1 to 100 nanojoules (nJ), a duration of 10 to 500 femtoseconds (fs), and a repetition rate of 1 to 100 megahertz (MHz). The laser device directs a laser beam comprising the subthreshold laser pulses along a laser beam path towards the target tissue by directing 10 to 100 subthreshold laser pulses towards the same target spot of the target tissue.

Embodiments may include none, one, some, or all of the following features:

The ophthalmic laser surgical system comprises an xy-scanner that: receives the detection beams from the target detection system and directs the detection beams along the detection beam path towards the xy-location of a target shadow cast by the target tissue onto the retina of the eye, the xy-location relative to an xy-scanner; and receives the laser beam from the laser device and directs the laser beam along the laser beam path aligned with the detection beam path towards the xy-location of the target shadow.

The target detection system comprises: an xy-location device that provides the xy-location of a target shadow of the target tissue, the xy-location related to an xy-scanner; and a z-location device that provides the z-location of the target tissue relative to the retina of the eye.

DESCRIPTION OF EXAMPLE EMBODIMENTS

Figure 1:
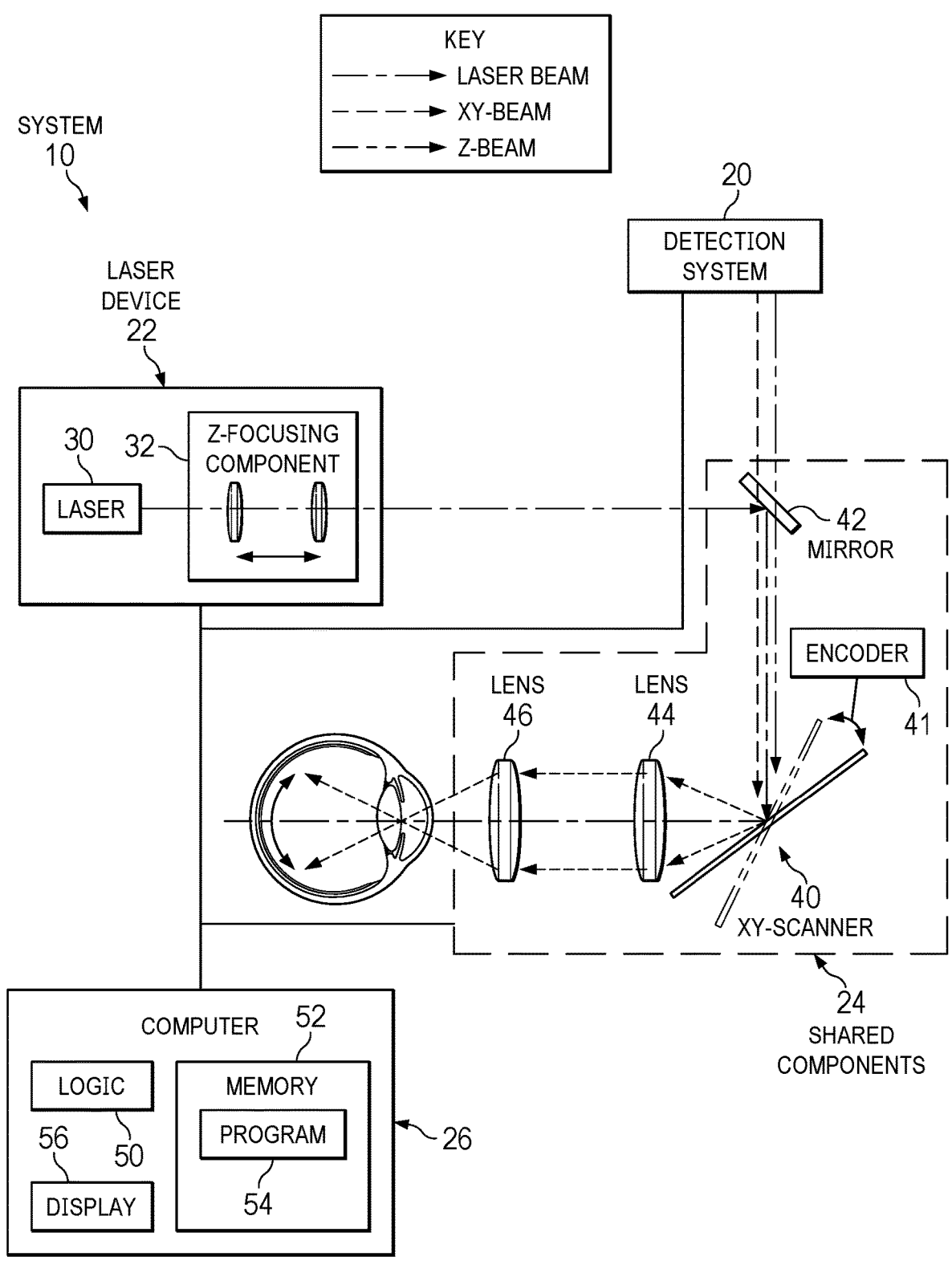
FIG. 1 illustrates an example of an ophthalmic laser surgical system that may be used to treat an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Known ophthalmic laser surgical systems include a YAG or femtosecond laser ("femto laser") that generates laser pulses to photodisrupt eye tissue. For example, YAG laser pulses with a 5 millijoule (mJ) pulse energy, 4 nanosecond (ns) pulse duration, and 1.064 micrometer (um) wavelength or femtosecond laser pulses with a 15 to 20 microjoule (uJ) pulse energy and 500 femtosecond (fs) pulse duration can photodisrupt tissue to create cavitation bubbles in the tissue.

However, YAG laser pulses cannot treat floaters closer than 10 millimeters (mm) to the retina without exceeding standard radiation exposure limits. Moreover, Chirped Pulse Amplification with Master Oscillator Power Amplifier (CPA MOPA) femto lasers are needed to produce the pulses that can photodisrupt tissue, and these lasers are prohibitively expensive for certain applications.

Accordingly, the surgical systems described herein include a femtosecond laser that produces subthreshold laser pulses. Subthreshold laser pulses have a pulse energy below the breakdown threshold of the tissue, i.e., the pulse energy at which optical breakdown occurs in the tissue. The pulses do not cause optical breakdown (photodisruption) or form cavitation bubbles. The lower pulse energy allows for destruction of floaters in more situations without overexposing the retina. Moreover, a femtosecond laser is much more affordable and reliable than a CPA MOPA femto laser.

FIG. 1 illustrates an example of an ophthalmic laser surgical system 10 that may be used to treat an eye, according to certain embodiments. Surgical system 10 may provide any suitable treatment where laser pulses are directed to a target tissue (e.g., vitreous floaters or vitreous-retinal traction fibers) in an eye. Examples of treatments include laser vitreolysis, traction fiber removal, and retinal microsurgery.

As an overview, system 10 includes a target detection system 20, a laser device 22, one or more shared components 24, and a computer 26, coupled as shown. Laser device 22 includes a laser 30 and a z-focusing component 32, coupled as shown. Shared components 24 include an xy-scanner 40, an xy-encoder 41, and optical elements (such as a mirror 42 and lenses 44 and 46), coupled as shown. Computer 26 includes logic 50, a memory 52 (which stores a computer program 54), and a display 56, coupled as shown. In certain embodiments, target detection system 20 and laser device 22 share xy-scanner 40, which allows target detection system 20 and laser device 22 to be co-registered. For ease of explanation, an axis (e.g., optical or visual axis) of the eye approximates a z-axis, which in turn defines enface planes (e.g., xy-planes) substantially orthogonal to the z-axis.

As an overview of operation of system 10, target detection system 20 directs detection beams along a detection beam path towards the target tissue in a vitreous of the eye, and determines the location of the target tissue within the vitreous. Laser device 22 comprises a femtosecond laser that generates subthreshold laser pulses with a pulse energy of 1 to 100 nanojoules (nJ). Laser device 22 directs a laser beam comprising the laser pulses along a laser beam path towards the target tissue.

Turning to the parts of the system, target detection system 20 includes one or more detection devices that detect, locate, and/or image a target tissue and/or a target shadow cast by the target tissue on the retina. To detect, locate, and/or image a target tissue and/or a target shadow, a detection device directs a detection beam along a detection beam path towards the interior of the eye. The interior reflects the detection beam, and the device detects the reflected light and detects, locates, and/or images a target tissue and/or a target shadow. In addition, the detection devices may provide the x, y, and/or z locations of the target tissue and/or a target shadow to another component. For example, an xy-location device provides the xy-location of the target shadow, and a z-location device provides the z-location of the target tissue.

The devices may utilize the same or different technologies (e.g., scanning laser ophthalmoscopy (SLO) and/or interferometry). In certain embodiments, a detection device is an SLO device that provides the xy-location of a target shadow. In certain embodiments, a detection device is an interferometer device with any suitable interferometer, e.g., a Fourier domain type (such as a swept source or a spectral domain type) that utilizes a fast Fourier transform (FFT). Examples of interferometer devices include an optical coherence tomography (OCT) device (such as a swept-source OCT device) and a swept source A-scan interferometer (SSASI) device. A SASSI device performs only A-scans.

Turning to laser device 22, laser 30 includes a femtosecond laser that produces subthreshold laser pulses to perform subthreshold laser surgery (SLS). In contrast, most femtosecond lasers used in ophthalmic surgery cut tissue with above-threshold pulses that cause photodisruption (or plasma mediated ablation). As an example of photodisruption, 3 microjoule (uJ), 500 femtosecond (fs) laser pulses are focused down to about 2 micrometer (um) spots. The peak intensity of the laser pulses at the focus is about 50 TW/cm$^2$ ($50*10^{12}$ W/cm$^2$) where W represents watt, TW represents terawatt, and cm represents centimeter.

At such extremely high laser intensities, multiphoton absorption can occur. The intensity removes electrons from atoms and molecules and creates a cloud of free electrons. The electric field of the laser pulses accelerate the free electrons by a process called inverse bremsstrahlung, and the accelerated free electrons ionize neutral atoms of the tissue in process called avalanche ionization. As a result of these processes, a high-density, high-temperature (e.g., approximately 5000K°) plasma is formed at the focus. The high-temperature plasma burns and evaporates a small (e.g., approximately 4 um×4 um×50 um) volume of tissue. The cascade of processes is known as breakdown. Breakdown threshold energy is the minimal laser pulse energy that can cause breakdown.

The high-temperature, high pressure vapors rapidly expand and form a cavitation bubble having a diameter of, e.g., about 200 um. The acceleration of the wall of a cavitation bubble (i.e., the vapor-tissue interface) can achieve an acceleration of $10^7$ m/s$^2$, i.e., approximately 1 million times free fall acceleration. The acceleration of bubble walls can also form shock waves in the tissue. The forces of acceleration and the shock waves tear apart a spherical volume of tissue having a diameter of approximately 100 to 200 um, which can be used to disintegrate tissue.

The high-temperature plasma, the rapidly expanding cavitation bubbles, and the shock wave may damage the retina if the focus is near the retina. For this reason, surgery with above-threshold laser pulses is not allowed to be performed very near to or at the surface of the retina. For example, surgery with above-threshold laser pulses is not allowed on the internal limiting membrane, epiretinal membrane, traction fibers connecting the hyaloid membrane and the retina, or retinal drusens.

Accordingly, the femtosecond laser of system 10 produces subthreshold laser pulses for subthreshold laser surgery (SLS), which may be performed closer to the retina as well as farther away. Subthreshold laser pulses have a pulse energy below the breakdown threshold of the tissue, e.g., a pulse energy of 1 to 100 nanojoules (nJ), such as a 50 nJ 500 fs laser pulse energy. The pulses do not cause an optical breakdown, form a high-density, high-temperature plasma, yield a cavitation bubble, or produce shock waves. However, subthreshold laser pulses can yield other effects that can disintegrate tissue. Moreover, several (e.g., greater than 5, e.g., 10) laser pulses may be spatially superimposed on top of each other at the same place at repetition rate of a few MHz to increase disintegration. Subthreshold laser pulses, even when superimposed, disintegrate the tissue locally, only substantially at the focus, so can be used for surgery near the retina.

Subthreshold laser pulses can cause the following effects that disintegrate tissue. Spatial superposition of laser pulses at the same spot can increase effects (1), (2), and (3) that can locally disintegrate tissue at the spot.

(1) Low-density free electrons. Subthreshold laser pulses can form a cloud of low-density free electrons that can trigger a chemical reaction that locally disintegrates tissue.

(2) Singlet oxygen molecules. Subthreshold laser pulses can form singlet oxygen molecules that are extremely chemically reactive.

(3) Multiphoton chemical reaction. Subthreshold laser pulses can cause a multiphoton chemical reaction that disintegrates tissue.

(4) Disruptive local thermoelastic strain. In an example, multiphoton absorption of a laser pulse can increase the temperature of tissue at the focus from, e.g., 37 to 47 centigrade. According to the temperature coefficient of the expansion of water, a focal volume of 2 um diameter may expand by 0.13%, i.e., by 0.0026 um. At a 500 fs rate, the expansion speed may be 0.0026 um/500 fs=5200 m/s. The speed of sound in the ophthalmic tissue is about 1500 m/s, so the expansion waves are supersonic. Accordingly, subthreshold laser pulses can cause supersonic, explosion-like transient thermoelastic waves that can tear ophthalmic tissue and cause local tissue disintegration of tissue.

Laser 30 generates a laser beam with any suitable wavelength, e.g., in an ultraviolet or infrared range. In certain embodiments, the pulses have a duration of 10 to 500 fs (e.g., 10 to 100, 100 to 200, 200 to 300, 300 to 400, and/or 400 to 500 fs), a pulse energy of 1 to 100 nanojoules (nJ) (e.g., 1 to 5, 5 to 25, 25 to 50, 50 to 75, and/or 75 to 100 nJ), and a repetition rate of 1 to 100 megahertz (MHz) (e.g., 1 to 40, 40 to 60, and/or 60 to 100 MHz). The same spot of the tissue may be exposed to a number N of laser pulses, where N is 10 to 100 (e.g., 10 to 40, 40 to 60, and/or 60 to 100) laser pulses. The number N of pulses at the same target spot may controlled by the repetition rate f of the laser, the xy-scanning speed v of the laser spot of the laser beam, and the target spot diameter d as $N=(d*f)/v$.

Z-focusing component 32 longitudinally directs the focal point of the laser beam to a specific location in the z-direction. Examples of z-focusing component 32 include a longitudinally adjustable lens, a lens of variable refractive power, an electrically or mechanically tunable lens (e.g., Optotune lens), an electrically or mechanically tunable telescope, or a deformable mirror that can control the z-location of the focal point. Z-focusing component 32 may direct the focal point in any suitable manner. In certain embodiments, z-focusing component 32 receives the z-location of the target tissue from target detection system 20 (and may receive it via computer 26), and directs the laser beam towards the z-location of the target tissue.

Shared components 24 direct detection and laser beams from target detection system 20 and laser device 22, respectively, towards the eye. Because detection and laser beams both use shared components 24, both beams are affected by the same optical distortions (e.g., fan distortion of scanners, barrel or pillow distortions of the scanner lens, refractive distortions from the inner eye surfaces, and other distortions). The distortions affect both beams in the same way, so the distortions are compensated for. This allows for aiming the laser beam using images generated by the detection beam with improved accuracy.

As an example of aiming the laser beam, an image of the eye may include a reticle, which is a graphical overlay (e.g., crosshairs) that indicates where the beam is currently aimed in an enface plane. The user or computer 26 may place the reticle over the target tissue in the image to aim the beam at the target tissue. Target detection system 20 provides the xy-location to xy-scanner 40. Xy-encoder 41 detects the position of xy-scanner 40 to determine the xy-location of the reticle (in encoder units) centered at the target tissue.

As an overview of operation of shared components 24, mirror 42 directs a beam (detection and/or laser beam) towards xy-scanner 40, which transversely directs the beam towards lens 44. Lenses 44 and 46 direct the beam towards eye. Shared components 24 may also provide spectral and polarization coupling and decoupling of detection and laser beams to allow the beams to share the same path.

Turning to the details of shared components 24, xy-scanner 40 transversely directs the focal point of the beam in the x- and y-directions. Xy-scanner 40 changes the angle of incidence of the beam into the pupil, allowing for the beam to cover a wider range within the eye. Xy-scanner 40 may transversely direct the beam in any suitable manner. For example, xy-scanner 40 may include a pair of galvanometrically-actuated scanner mirrors that can be tilted about mutually perpendicular axes. As another example, xy-scanner 40 may include an electro-optical crystal that can electro-optically steer the beam or an acousto-optical crystal that can acousto-optically steer the beam. As another example, xy-scanner 40 may include a fast scanner that can create, e.g., a 3D matrix of laser pulses. Examples of such scanners include a galvo scanner, resonant scanner, or acousto optical scanner. In certain embodiments, xy-scanner 40 receives the xy-location of the target shadow from target detection system 20, and directs the detection and/or laser beam towards the xy-location.

Xy-encoder 41 detects the position of xy-scanner 40 and reports the position as the xy-location. For example, xy-encoder 41 detects the angular orientations of the galvanometer mirrors of xy-scanner 40 in encoder units. Xy-encoder 41 may report the position in encoder units to target detection system 20, laser device 22, and/or computer 26. Since target detection system 20 and laser device 22 share xy-scanner 40, computer 26 can use the encoder units to instruct system 20 and device 22 where to aim their beams, making it unnecessary to perform the computer-intensive conversion from encoder units to a length unit such as millimeters. Xy-encoder 41 may report the positions at any suitable rate, e.g., once every 5 to 50 milliseconds (ms), such as every 10 to 30 or approximately every 20 ms.

Shared components 24 also include optical elements. In general, an optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical elements include mirror 42 and lenses 44 and 46. Mirror 42 may be a trichroic mirror. Lenses 44 and 46 may be scanning optics of an SLO device.

Computer 26 controls components of system 10 (e.g., target detection system 20, laser device 24, and/or shared components 24) in accordance with a computer program 54. Computer 26 may be separated from components or may be distributed among system 10 in any suitable manner, e.g., within target detection system 20, laser device 24, and/or shared components 24. In certain embodiments, portions of computer 26 that control target detection system 20, laser device 24, and/or shared components 24 may be part of target detection system 20, laser device 24, and/or shared components 24, respectively.

Computer 26 controls the components of system 10 in accordance with a computer program 54. Examples of computer programs 54 include target imaging, target tracking, image processing, target evaluation, retinal exposure calculation, patient education, and insurance authorization programs. For example, computer 26 may use a computer program 54 to instruct target detection system 20, laser device 24, and/or shared components 24 to image a target tissue and focus a laser beam at the target tissue.

In certain embodiments, computer 26 uses an image processing program 54 to perform image processing on an image, e.g., analyze the digital information of the image to extract information from the image. In certain embodiments, image processing program 54 analyzes an image of a target tissue or a target shadow to obtain information about the target tissue. For example, program 54 may detect a target shadow by detecting a darker shape in an image (using, e.g., edge detection or pixel analysis). As another example, program 54 may detect the shape and size of a target shadow, which indicate the size and shape of the target tissue. As another example, program 54 may detect the tone or luminescence of the target shadow, which indicates the density of the target tissue.

In certain embodiments, computer 26 uses a target evaluation and diagnosis program 54 to evaluate a target tissue, such as a floater, to determine if the target tissue is clinically significant, i.e., affects vision. In certain embodiments, display 56 of computer 26 displays images (such as a video) of a target shadow so a user can evaluate the target tissue. In other embodiments, computer 26 uses image processing to evaluate the target tissue. Target evaluation and diagnosis are as described in more detail with reference to FIG. 2.

Figure 2:
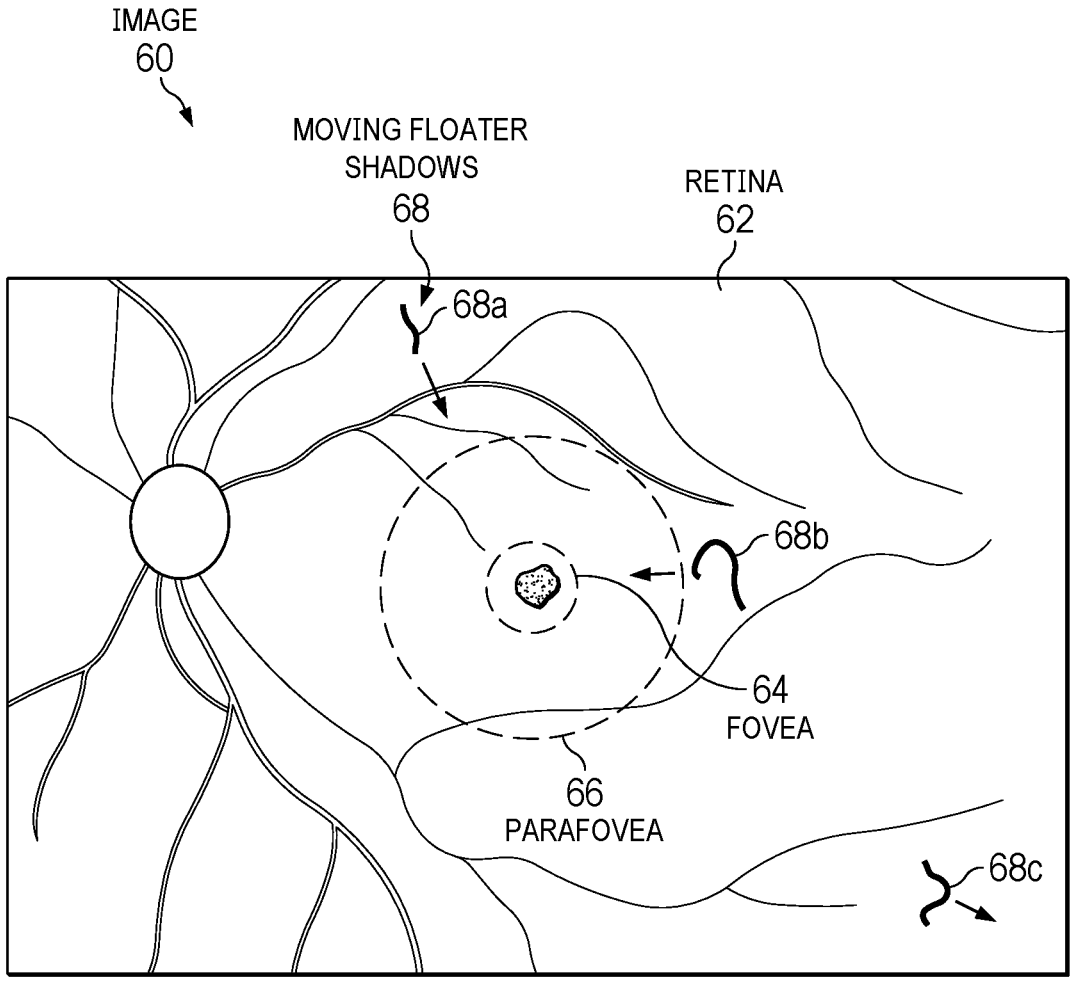
FIG. 2 illustrates an example of a retinal image that may be generated by the system of FIG. 1.

FIG. 2 illustrates an example of a retinal image 60 that may be generated by system 10 of FIG. 1. Image 60 shows the retina 62 of an eye, with a foveal region (or fovea) 64 and a parafoveal region (or parafovea) 66. Generally, fovea 64 has a visual angle of approximately +/− one degree, and parafovea 66 has a visual angle of approximately +/− seven degrees. Image 60 also shows floater shadows 68 (68*a*, 68*b*, 68*c*) that floaters cast on retina 62. In general, non-moving shadows are not caused by floaters, and may be caused by, e.g., corneal or lens opacities or anatomical changes of the retina, so floater treatment is not concerned with non-moving shadows.

A floater may be regarded as clinically significant if it can cause a visual disturbance, which can be determined from any suitable features of the floater shadow, e.g., the size and/or density of the shadow, proximity of the shadow to the fovea and/or parafovea, and/or the track of the shadow relative to the fovea and/or parafovea. As an example, a floater can cause a visual disturbance if it permanently or transiently casts a shadow 68 on fovea 64 or can cause distraction or annoyance if it permanently or transiently casts a shadow 68 on parafovea 66. Accordingly, if a floater shadow falls within or is predicted to move within fovea 64 and/or parafovea 66, the floater may be designated as clinically significant. As another example, floater shadow 68 can be used to estimate the size and density of the floater. Larger, denser floaters are more likely to cause a visual disturbance. Thus, a shadow 68 larger than a critical shadow size can indicate a clinically significant floater. A shadow 68 with a higher contrast relative to the background may indicate a clinically significant floater.

Figure 3:
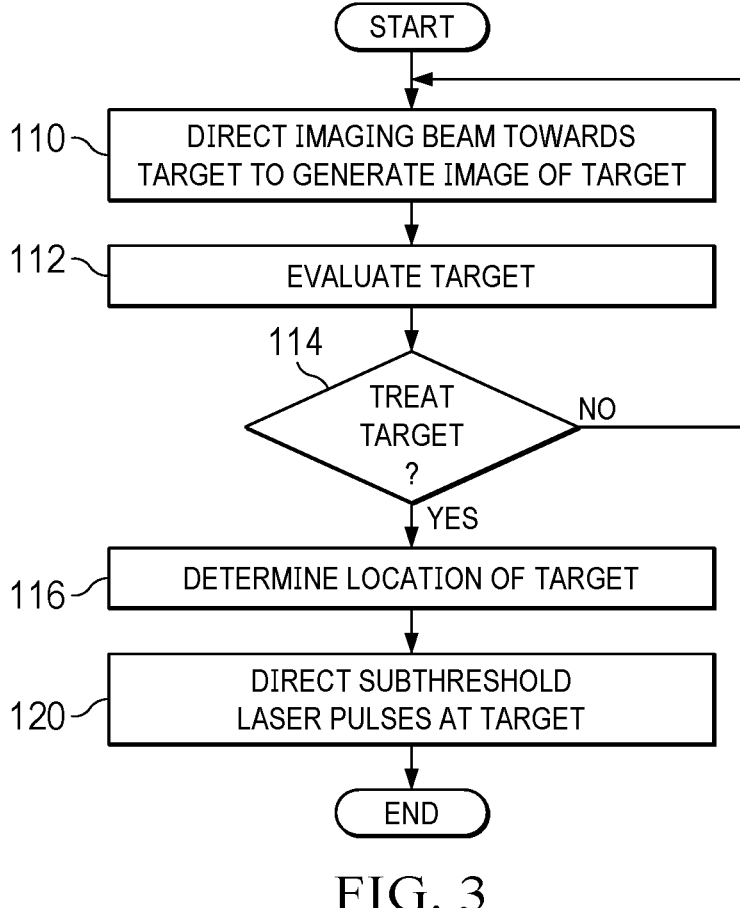
FIG. 3 illustrates an example of a method for treating a target tissue in an eye that may be performed by the system of FIG. 1, according to certain embodiments.

FIG. 3 illustrates an example of a method for treating a target tissue in an eye that may be performed by system 10 of FIG. 1, according to certain embodiments. The method starts at step 110, where the target detection system directs a detection beam towards the target tissue shadow to generate an image of the target shadow.

The target tissue is evaluated as to whether it should be treated at step 112. The evaluation may evaluate the target shadow to determine the location, size, shape, and/or density of the target tissue. The target tissue may be treated at step 114. If the target tissue is not to be treated, the method returns to step 110 to continue generating images of the target tissue. If the target tissue is to be treated, the method proceeds to step 116, where the target detection system is used to determine the location of the target shadow.

Subthreshold laser pulses are directed at the target tissue at step 120 to treat (e.g., fragment) the target tissue. Subthreshold laser pulses have a pulse energy below the breakdown threshold of the tissue, so do not cause photodisruption. The pulses treat the target tissue by exposing the same spot to a number N of laser pulses, where N is 10 to 100, to fragment and remove the target tissue.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser surgical system for treating a target tissue in an eye, comprising:
    a target detection system configured to:
        direct one or more detection beams along a detection beam path towards the target tissue in a vitreous of the eye, the target tissue having an optical breakdown threshold; and
        determine a location of the target tissue within the vitreous based on a target shadow cast by the target tissue onto a retina of the eye; and
    a laser device comprising a femtosecond laser configured to generate a plurality of subthreshold laser pulses, the subthreshold laser pulses having a pulse energy below the optical breakdown threshold of the target tissue, the laser device configured to:
        direct a laser beam comprising the plurality of subthreshold laser pulses along a laser beam path towards the target tissue.

2. The ophthalmic laser surgical system of claim 1, further comprising an xy-scanner configured to:
    receive the one or more detection beams from the target detection system and direct the one or more detection beams along the detection beam path towards an xy-location of the target shadow, the xy-location relative to the xy-scanner; and
    receive the laser beam from the laser device and direct the laser beam along the laser beam path aligned with the detection beam path towards the xy-location of the target shadow.

3. The ophthalmic laser surgical system of claim 1, wherein the pulse energy is 1 to 100 nanojoules (nJ).

4. The ophthalmic laser surgical system of claim 1, the subthreshold laser pulses having a duration of 10 to 500 femtoseconds (fs).

5. The ophthalmic laser surgical system of claim 1, the subthreshold laser pulses having a repetition rate of 1 to 100 megahertz (MHz).

6. The ophthalmic laser surgical system of claim 1, the laser device configured to direct the laser beam comprising the plurality of subthreshold laser pulses by directing 10 to 100 subthreshold laser pulses towards a same target spot of the target tissue.

7. The ophthalmic laser surgical system of claim 6, wherein a number N of subthreshold laser pulses at the same target spot is controlled by a repetition rate f of the laser device, an xy-scanning speed v of a laser spot of the laser beam, and a target spot diameter d according to $N=(d*f)/v$.

8. The ophthalmic laser surgical system of claim 1, the laser device comprising a z-focusing component configured to:
    receive a z-location of the target tissue relative to the retina of the eye; and
    direct a focal point of the laser beam towards the z-location of the target tissue.

9. The ophthalmic laser surgical system of claim 1, the target detection system comprising:
    an xy-location device configured to provide an xy-location of the target shadow of the target tissue, the xy-location related to an xy-scanner; and
    a z-location device configured to provide a z-location of the target tissue relative to the retina of the eye.

10. The ophthalmic laser surgical system of claim 9, the xy-location device comprising a scanning laser ophthalmoscopy (SLO) device.

11. The ophthalmic laser surgical system of claim 9, the z-location device comprising an interferometer device.

12. The ophthalmic laser surgical system of claim 1, the target tissue comprising a vitreous-retinal traction fiber.

13. The ophthalmic laser surgical system of claim 1, the target tissue comprising a vitreous floater.

14. The ophthalmic laser surgical system of claim 1, the laser beam configured to:
    form a cloud of low-density free electrons using the plurality of subthreshold laser pulses to trigger a chemical reaction that locally disintegrates a portion of the target tissue.

15. The ophthalmic laser surgical system of claim 1, the laser beam configured to:
    form a plurality of singlet oxygen molecules using the plurality of subthreshold laser pulses to cause a chemical reaction within a portion of the target tissue.

16. The ophthalmic laser surgical system of claim 1, the laser beam configured to:
    cause a multiphoton chemical reaction using the plurality of subthreshold laser pulses to locally disintegrate a portion of the target tissue.

17. The ophthalmic laser surgical system of claim 1, the laser beam configured to:
    cause a supersonic thermoelastic wave using the plurality of subthreshold laser pulses to locally disintegrate a portion of the target tissue.

18. An ophthalmic laser surgical system for treating a target tissue in an eye, comprising:
    a target detection system configured to:
        direct one or more detection beams along a detection beam path towards the target tissue in a vitreous of the eye, the target tissue having an optical breakdown threshold; and
        determine a location of the target tissue within the vitreous based on a target shadow cast by the target tissue onto a retina of the eye; and a laser device comprising a femtosecond laser configured to generate a plurality of subthreshold laser pulses, the subthreshold laser pulses having a pulse energy below the optical breakdown threshold of the target tissue, the pulse energy is 1 to 100 nanojoules (nJ), the subthreshold laser pulses having a duration of 10 to 500 femtoseconds (fs) and a repetition rate of 1 to 100 megahertz (MHz), the laser device configured to:

direct a laser beam comprising the plurality of subthreshold laser pulses along a laser beam path towards the target tissue by directing 10 to 100 subthreshold laser pulses towards a same target spot of the target tissue.

19. The ophthalmic laser surgical system of claim 18, further comprising an xy-scanner configured to:

receive the one or more detection beams from the target detection system and direct the one or more detection beams along the detection beam path towards an xy-location of the target shadow, the xy-location relative to the xy-scanner; and receive the laser beam from the laser device and direct the laser beam along the laser beam path aligned with the detection beam path towards the xy-location of the target shadow.

20. The ophthalmic laser surgical system of claim 18, the target detection system comprising:

an xy-location device configured to provide an xy-location of the target shadow of the target tissue, the xy-location related to an xy-scanner; and a z-location device configured to provide a z-location of the target tissue relative to the retina of the eye.

\* \* \* \* \*